(12) United States Patent
Erickson et al.

(10) Patent No.: US 10,040,551 B2
(45) Date of Patent: Aug. 7, 2018

(54) DRONE DELIVERY OF COFFEE BASED ON A COGNITIVE STATE OF AN INDIVIDUAL

(71) Applicant: International Business Machines Corporation, Armonk, NY (US)

(72) Inventors: Thomas David Erickson, Minneapolis, MN (US); Rogerio S. Feris, Hartford, CT (US); Clifford A. Pickover, Yorktown Heights, NY (US); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 101 days.

(21) Appl. No.: 14/978,620

(22) Filed: Dec. 22, 2015

(65) Prior Publication Data
US 2017/0174343 A1 Jun. 22, 2017

(51) Int. Cl.
*E04H 3/04* (2006.01)
*B64C 39/02* (2006.01)
(Continued)

(52) U.S. Cl.
CPC .............. *B64C 39/024* (2013.01); *A61B 5/01* (2013.01); *A61B 5/02055* (2013.01); *A61B 5/11* (2013.01);
(Continued)

(58) Field of Classification Search
CPC .......... A61B 5/1176; A61B 2034/2057; A61B 2034/2065; A61B 5/165; A61B 5/02055;
(Continued)

(56) References Cited

U.S. PATENT DOCUMENTS

| 5,094,153 A | 3/1992 | Helbling |
| 6,419,629 B1 | 7/2002 | Balkin et al. |

(Continued)

FOREIGN PATENT DOCUMENTS

| WO | 0117362 | 3/2001 |
| WO | 2005000385 | 1/2005 |

OTHER PUBLICATIONS

Disclosed Anonymously, "Use of Flavors with Modifying Properties (FMP) in Flavor Compositions and Applications of FMP in Food and Beverage Products", IP.com No. 000240463, Jan. 30, 2015, pp. 1-43.

(Continued)

*Primary Examiner* — Jeffrey A Shapiro
(74) *Attorney, Agent, or Firm* — Fleit Gibbons Gutman Bongini Bianco PL; Gary Winer (57) ABSTRACT

Coffee or other drink, for example a caffeine containing drink, is delivered to individuals that would like the drink, or who have a predetermined cognitive state, using an unmanned aerial vehicle (UAV)/drone. The drink is connected to the UAV, and the UAV flies to an area including people, and uses sensors to scan the people for an individual who has gestured that they would like the drink, or for whom an electronic analysis of sensor data indicates to be in a predetermined cognitive state. The UAV then flies to the individual to deliver the drink. The analysis can include profile data of people, including electronic calendar data, which can be used to determine a potentially predetermined cognitive state.

17 Claims, 4 Drawing Sheets

(51) Int. Cl.

| | |
|---|---|
| A61B 5/16 | (2006.01) |
| A61B 5/0205 | (2006.01) |
| A61B 5/01 | (2006.01) |
| A61B 5/1171 | (2016.01) |
| A61B 5/11 | (2006.01) |
| A61B 5/024 | (2006.01) |
| A61B 5/021 | (2006.01) |
| A61B 5/08 | (2006.01) |
| A61B 3/11 | (2006.01) |

(52) U.S. Cl.
CPC ............ *A61B 5/1176* (2013.01); *A61B 5/165* (2013.01); *A61B 3/112* (2013.01); *A61B 5/021* (2013.01); *A61B 5/024* (2013.01); *A61B 5/082* (2013.01); *B64C 2201/024* (2013.01); *B64C 2201/128* (2013.01); *B64C 2201/141* (2013.01)

(58) Field of Classification Search
CPC .. A61B 5/01; A61B 5/11; A61B 5/024; A61B 5/128; A61B 5/141; A61B 5/021; A61B 5/082; A61B 3/112; G06F 3/013; G06K 9/00221; G06K 9/00248; G06K 9/00302; G06K 9/00315; G06K 9/00308; G06K 7/00; G06K 7/10; G06T 2207/30201; H04N 5/23219; B64C 2201/00; B64C 2201/02; B64C 2201/022; B64C 2201/024; B64C 2201/027; B64C 2201/028; B64C 2201/04; B64C 2201/042; B64C 2201/044; B64C 2201/046; B64C 2201/048; B64C 2201/06; B64C 2201/063; B64C 2201/066; B64C 2201/08; B64C 2201/082; B64C 2201/084; B64C 2201/086; B64C 2201/088; B64C 2201/10; B64C 2201/101; B64C 2201/102; B64C 2201/104; B64C 2201/105; B64C 2201/107; B64C 2201/108; B64C 2201/12; B64C 2201/121; B64C 2201/122; B64C 2201/123; B64C 2201/125; B64C 2201/126; B64C 2201/127; B64C 2201/128; B64C 2201/14; B64C 2201/143; B64C 2201/145; B64C 2201/146; B64C 2201/148; B64C 2201/16; B64C 2201/162; B64C 2201/165; B64C 2201/167; B64C 2201/18; B64C 2201/182; B64C 2201/185; B64C 2201/187; B64C 2201/20; B64C 2201/201; B64C 2201/203; B64C 2201/205; B64C 2201/206; B64C 2201/208; B64C 2201/22; E04H 3/00; E04H 3/02; E04H 3/04; E04H 14/00; A47F 9/046; A47F 9/00; A47F 3/00; A47F 1/06; A47F 1/08; A47F 1/12; A47F 3/04; A47F 1/035; A47F 9/04; B07C 3/087; B65G 35/00
USPC ............ 382/103, 104, 115, 118; 186/35, 36, 186/38–40, 51, 52, 55, 56, 7, 26
See application file for complete search history.

(56) References Cited

U.S. PATENT DOCUMENTS

| | | | |
|---|---|---|---|
| 7,350,455 B2 | 4/2008 | Vetterli | |
| 7,384,394 B2 | 6/2008 | Hursh et al. | |
| 8,157,205 B2* | 4/2012 | McWhirk | B64B 1/02 212/274 |
| 8,171,843 B1 | 5/2012 | Heffington | |
| 8,509,947 B2 | 8/2013 | Jarisch et al. | |
| 9,022,322 B2* | 5/2015 | Westbrook, Sr. | B64C 39/024 244/137.1 |
| 9,044,543 B2 | 6/2015 | Levien et al. | |
| 9,321,531 B1* | 4/2016 | Takayama | B64D 1/12 |
| 2005/0102246 A1* | 5/2005 | Movellan | G06K 9/00248 706/12 |
| 2009/0152391 A1* | 6/2009 | McWhirk | B64B 1/02 244/30 |
| 2010/0033333 A1* | 2/2010 | Victor | A61B 3/113 340/576 |
| 2011/0313014 A1* | 12/2011 | Robert | A23F 5/14 514/419 |
| 2012/0175468 A1 | 7/2012 | Zerof | |
| 2012/0298676 A1* | 11/2012 | Cooks | B65D 1/04 220/592.21 |
| 2013/0103195 A1* | 4/2013 | Anhalt | B25J 9/163 700/248 |
| 2013/0253733 A1* | 9/2013 | Lee | B64C 19/00 701/2 |
| 2014/0067160 A1 | 3/2014 | Levien et al. | |
| 2014/0152792 A1* | 6/2014 | Krueger | G01C 23/00 348/78 |
| 2014/0353422 A1* | 12/2014 | Westbrook, Sr. | B64C 39/024 244/17.21 |
| 2014/0371912 A1 | 12/2014 | Passot et al. | |
| 2015/0046018 A1* | 2/2015 | Hayashi | G05D 1/0088 701/26 |
| 2016/0068264 A1* | 3/2016 | Ganesh | G08G 5/0069 701/2 |
| 2016/0189101 A1* | 6/2016 | Kantor | G08G 5/0013 705/338 |
| 2016/0236778 A1* | 8/2016 | Takayama | B64D 1/12 |

OTHER PUBLICATIONS

Disclosed Anonymously, "Storage Area Network Relocation Utilizing Drones", IP.com No. 000242096, Jun. 18, 2015, pp. 1-3.
Smarthome, "Beyond Coffee Maker", http://www.smarthome.com/beyond-coffee-maker.html, last visited on Nov. 17, 2015, p. 1.
AZ Central, "Coffee is a $30 Billion-a-Year U.S. Industry—and it's Growing", http://archive.azcentral.com/business/consumer/articles/20130410coffee-is-a-billionayear-us-industry-and-its-growing.html, last visited on Nov. 17, 2015, pp. 1-2.
Crane, E., "Is this the Office of the Future? Workplaces may Feature Coffee Delivered by Drones, Holographic Employees, and Robots", DailyMail.com, Feb. 5, 2015, http://www.dailymail.co.uk/news/article-2940535/Is-office-future-Innovative-report-says-coffee-delivered-drones-employees-holographic-25-years.html, pp. 1-5.
The Beverage Journal, "Drone Delivery Takes Wing for Milford's Tilted Kilt", Aug. 30, 2014, http://www.thebeveragejournal.com/tag/drone-delivery, pp. 1-2.
Business Insider, "Here's Why Venture-Capital Firms and Major Global Companies are Investing in Drone Startups", Nov. 6, 2015, http://www.businessinsider.com/drones-report-market-entrants-2015-3, pp. 1-3.
Lifehacker, "Five Best Sleep Tracking Gadgets or Apps", Mar. 31, 2013, http://lifehacker.com/5993005/five-best-sleep-tracking-gadgets-or-apps?tag=hive-five, pp. 1-9.
Hof, K., "If Lattes Could Fly: Dutch Engineers Invent Coffee Delivery Drone", Sprudge, Dec. 8, 2014, http://sprudge.com/coffee-drone-delivery-coffee-virus-amsterdam-a-lab-67046.html, pp. 1-14.
Eugenios, J., "What Would you Pay for a Drone Bartender?" CNN Money, Jun. 3, 2014, http://money.cnn.com/2014/06/03/luxury/drone-drinks, pp. 1-4.
Henry, A., "Sleep Time Alarm Clock for Android Watches Your Sleep Cycles, Wakes You Gently", Lifehacker, Sep. 12, 2012, Lifehacker, http://lifehacker.com/5942519/sleep-time-alarm-clock-for-android-watches-your-sleep-cycles-wakes-you-gently, pp. 1-2.
Contrera, J., "Apptitude: Up Coffee Helps Track Caffeine Intake", The Washington Post, Sep. 12, 2014, http://www.washingtonpost.

(56) References Cited

OTHER PUBLICATIONS com/lifestyle/magazine/apptitude-up-coffee-helps-track-caffeine-intake/2014/09/10/1f3e79e4-0c52-11e4-8341-b8072b1e7348_story.html, pp. 1-3.

Welsh, E.J., et al., "The Effect of Caffeine in People with Asthma", Cochrane Database of Systematic Reviews, Aug. 11, 2011, pp. 1-2, Issue 1.

Watson, E., "Packaged Facts: Younger adults might be immersed in the coffee house culture, but they don't drink as much coffee as we think", May 6, 2014, http://www.foodnavigator-usa.com/Markets/Packaged-Facts-2014-US-retail-foodservice-coffee-market-report, pp. 1-4.

Drugs.com, "Caffeine Drug Interactions", http://www.drugs.com/drug-interactions/caffeine.html%5D, last visited on Dec. 21, 2015, pp. 1-2.

Taigman, Y., et al., "DeepFace: Closing the Gap to Human-Level Performance in Face Verification" IEEE Conference on Computer Vision and Pattern Recognition, Jun. 23-28, 2014, pp. 1-8.

Wikipedia, "Gesture Recognition", https://en.wikipedia.org/wiki/Gesture_recognition, last visited on Dec. 21, 2015, pp. 1-8.

\* cited by examiner

DRONE DELIVERY OF COFFEE BASED ON A COGNITIVE STATE OF AN INDIVIDUAL

FIELD OF THE DISCLOSURE

The disclosure relates to a system and method for using drones to deliver a drink to an individual, and more particularly, sensing a predetermined cognitive state of an individual to identify a candidate for delivery of a drink.

BACKGROUND OF THE DISCLOSURE

Quick and easy delivery of drinks is a new way of service around the world. Drone technology has increased to support delivery of packages around the world. Drone technology can also assist in customer service areas. Drones that are functioned to deliver products have yet to deliver beverages based on the person(s) being served to.

SUMMARY OF THE DISCLOSURE

In an embodiment of the disclosure, a method for delivering a drink to an individual comprises connecting the drink to an unmanned aerial vehicle (UAV); flying the UAV to an area including a plurality of people; scanning the people, using one or more sensors connected to the UAV, the one or more sensors connected to an electronic processing circuit which identifies an individual among the people that may have a predetermined cognitive state, based on sensor data; and flying the UAV to the individual that may have a predetermined cognitive state to deliver the drink to the individual.

In another embodiment of the disclosure, a method for delivering a drink to an individual comprises connecting at least one coffee drink to a fully autonomous unmanned aerial vehicle (UAV); the UAV autonomously flying to an area including a plurality of people; scanning the people, using one or more sensors connected to the UAV, the one or more sensors connected to an electronic processing circuit which identifies an individual among the people that may have a predetermined cognitive state, or that has indicated by a gesture that a drink is wanted, based upon sensor data; processing by the electronic processing circuit to determine that the individual is eligible for delivery of the drink; and the UAV autonomously flying to the individual that may have a predetermined cognitive state or who has gestured, to deliver the drink to the individual.

In a further embodiment of the disclosure, a system for delivering a drink to an individual, comprises at least one fully autonomous unmanned aerial vehicle (UAV); a drink holder connected to each of the at least one UAV; at least one sensor including at least a camera connected to the UAV; and at least one electronic processing circuit connected to obtain data from the at least one sensor, the circuit configured to use data from the sensors, including scanning images from the camera, to identify an individual that may have a predetermined cognitive state, or that has indicated by a gesture that a drink is wanted, based upon the sensor data, and to thereby cause the UAV to fly to the individual to deliver a drink to the individual from the drink holder.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE DISCLOSURE

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

Over 80% of American adults now drink coffee, and this trend is growing, with many people drinking multiple cups of coffee per day. The present disclosure provides a method and system for assessing the cognitive state of one or more potential recipients for coffee, and delivering the coffee to them using a flying drone. More specifically, the drone can assess the cognitive state of an individual with a corresponding confidence level (L). Based on that assessment and the value of L, the drone proactively and automatically delivers coffee to one or more recipients, for example who are in a large office complex. The assessment and estimate is based on any of: sleep quality (e.g. assessed by known methods), electronic calendar (e.g. time of day, schedule of meetings, nature of attendees at meetings, analysis of size and interaction state of a group, complexity of work schedule and topic), biometrics, blood pressure, pupil dilation, facial expression analysis, the time an individual woke up in morning, and gesture analysis. Other factors can be assessed and used in a decision to deliver coffee to an individual. In this disclosure, individuals within a group of individuals served by drones are termed 'users' of system 100, although their participation can be entirely passive.

The drone also orchestrates the delivery of one or more coffee beverages or drinks along a route to fulfill the needs of small groups (that would wish to be served in one service), and/or to stimulate demand by providing coffee to clients who are in the view of others. The delivery may be triggered when (L>threshold) and/or the number of nearby potential recipients exceeds N. That is, if one prospective recipient turns down the offering of coffee, another nearby person may be potentially interested and offered the prepared and ready coffee. A human might also use a gesture like beaconing or waving to indicate interest, which could adjust the level of L.

Coffee consumption often has a habitual or ritualistic aspect to it, with many individuals having coffee to start their day, punctuate a mid-morning break, or as an after dinner activity. Over time, a system of the disclosure can learn times and places at which an individual tends to prefer to consume coffee, and can use that history to adjust its estimate of L for a particular person or place.

It is also the case that coffee consumption is enjoyed by people in groups. Coffee consumption can be a semi-ritualistic activity performed by a small group, and can also be an activity preferred in public, for example in a venue such as a coffee shop or salon.

In the small group context, coffee consumption can be a social practice that assists various social roles, such as easing introductions or casual conversation (ice-breaking), and for providing a change in pace (a coffee break) for an interacting group. Thus, in accordance with the disclosure, it is desirable to assess the state of the group and its interaction, including and or all of: (i) an amount of time since the group interaction began; (ii) a nature of the interaction, which can be any of a casual conversation, intense discussion, low-energy interaction, or anger or another dysfunctional interaction; and (iii) the size of the group.

With respect to item (iii), it may be preferable for one or more coffee delivery drones to deliver sufficient coffee to serve an entire group within a reasonable time period, to avoid awkwardness or discomfort associated with appearing to not serve certain group members, or by creating multiple interruptions in the group activity for coffee delivery. In an embodiment, one drone may summon another drone to fulfill an unexpectedly large demand for coffee.

The result of an analysis of items (i) to (iii) can contribute to the value of L.

If it is desired to increase consumption of coffee, and if coffee delivery and consumption is carried out in a public location where it is visible to others, social psychology suggests that the public nature of the serving and consumption will stimulate others to desire coffee in a phenomenon know as "social proof", or informational social influence. If a coffee drone has a dwindling supply of coffee, social psychology again suggests that the dwindling of the supply would increase the desirability of the coffee, and this could be leveraged by either summoning a second coffee drone to supply the stimulated need, and/or by allowing others to bid for the remaining coffees. A coffee drone in this setting might also take advantage of social psychological effects by first providing coffee to a person who is popular, famous, or otherwise has a high social status, as social proof is known to be magnified by such factors.

Finally, both the phenomenon of social proof, and the social desirability of fulfilling the needs of an interacting group in one delivery event, suggest that a coffee delivery drone would also benefit from the ability to orchestrate deliveries with the needs of a group in mind.

Of course, potential recipients may have preference profiles. For added utility, the disclosure provides for drinks which can be milk-based drinks or filter coffees. With respect to the latter, in particular, rapid transportation is useful, as these drinks tend to develop their flavor pattern as they cool down.

A system 100 of the disclosure includes at least one unmanned aerial vehicle (UAV) or drone 200, and an optional server 700. At least one of the drones 200 and servers 700 have an electronic processing circuit configured to execute machine instructions to carry out the tasks described herein. Drone 200 and server 700 are configured to communicate with each other wirelessly during flight operation of drone 200, for example using a short or long range wireless communication protocol 280, examples including WiFi, WiMAX, BLUETOOTH, SIGFOX, 3G, 4G, LTE, or another protocol, for example using a publicly available frequency, diagrammatically illustrated in FIG. 1. Drone 200 can have varying amounts of processing capability, but includes at least sufficient processing capacity to fly, and further includes the components normally associated with a UAV, such as a means of propulsion, for example one or more propellers 202 driven by a motor 204, a battery 206, one or more cameras 206, a control circuit 210 including flight related sensors and electronics and software, and communications electronics, including wireless two way communication for remote or semi-autonomous control, although drones of the disclosure can be implemented as fully autonomous.

Figure 1:
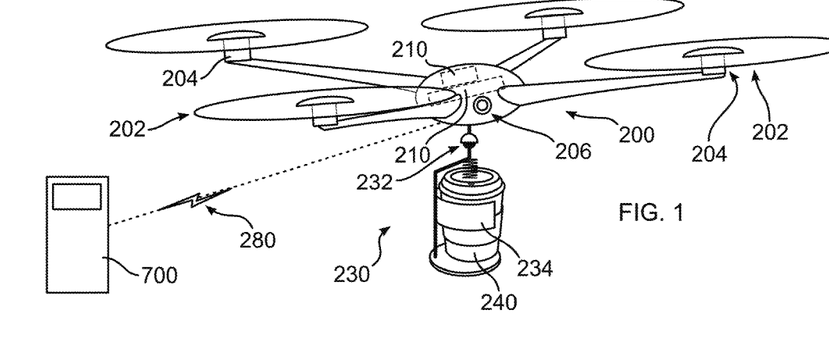
FIG. 1 depicts, an unmanned aerial vehicle (UAV)/drone of the disclosure carrying coffee in a drink holder, the drone in communication with a server, the drone including one or more sensors.

A four propeller drone is illustrated, although any drone configuration that can fly within an anticipated area of deployment can be used, provided it has sufficient strength to deliver coffee in the volumes required. For clarity, propeller guards are not illustrated. However, it should be understood that safety equipment should be provided, particularly as drone 200 is expected to fly near humans. Likewise, while any size drone can be used, it should not be larger than required for the intended mission as described herein, to reduce potential harm due to collision or other failure.

Figure 2:
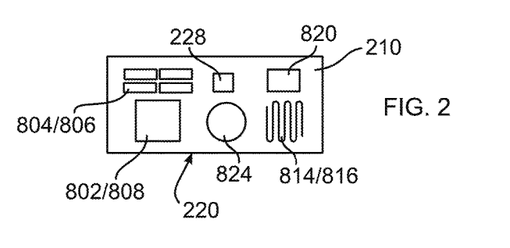
FIG. 2 depicts a diagram of a control circuit within the drone, the control circuit including electronic circuits for flying the drone, communicating with the server, storing and accessing data, saving a processing state, and processing data.

Control circuit 210 is diagrammatically illustrated in FIG. 2, and as mentioned, includes electronics 228 necessary to carry out flight in accordance with an intended mission, whether that is remote piloted, semi-autonomous, or fully autonomous. In an embodiment of the disclosure, drone 200 can carry out all processing tasks described herein relating to recognizing users, selecting drinks, delivering drinks, and identifying a cognitive state of humans. However, it should be understood that such tasks can be shared or divided between drone 200 and server 700 as desired, using wireless transmission of data between drone 200 and server 700.

Other components of control circuit include non-transitory memory 224 coupled to an electronic processor circuit, such as a microprocessor 802 and/or a digital signal processor 808, a battery to preserve a configuration state, one or more antennas 814/816. These components, as well as numerous other components not shown in FIG. 2, are described in more detail with respect to FIGS. 7 and 8.

The drone additional includes a coffee holder 230 which can have any of a variety of configurations. In the embodiment shown in FIG. 1, a gimbal joint 232 for enabling the coffee to remain upright as drone 200 pivots during flight, and a clamp 234 for retaining the coffee drink 240 upon the holder 230, the coffee drink 240 having the form, here, of a liquid retained within a cup having a lid. In another embodiment, the coffee can be retained within a container inside drone 200, and can be dispensed in liquid form directly from the drone. Accompaniments, such as sugar, sweetener, milk, and the like, can be dispensed in a similar manner, for example from a tube, the release of substance dispensed through the tube under control of drone 200.

Figure 3:
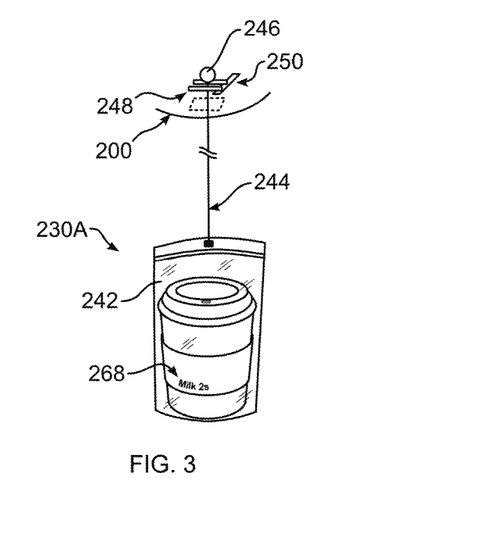
FIG. 3 depicts a drink holder and dispensing system of the disclosure, the holder and dispenser connectable to a drone of the disclosure.
Figure 4:
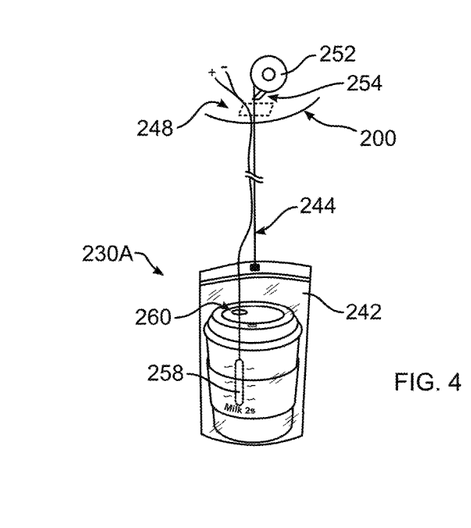
FIG. 4 depicts a variation of a drink holder and dispensing system of the disclosure, the holder and dispenser connectable to a drone of the disclosure.

In FIG. 3, an alternative coffee holder 230A is illustrated. In this embodiment, coffee drink 240 is retained within a leak proof 242 that is sufficiently strong to retain the coffee in the event the coffee is accidentally dropped from the drone before delivery. If bag 242 is transparent, it may be possible to read indicia 268 printed upon the cup of coffee drink 240 indicative of the style of coffee and the ingredients which have been added. A string 244 is connected to bag 242, the string extending to the drone to support drink 240 within bag 242 during flight and before delivery. String 244 can be connected to drone 200 in any known manner, however in the embodiment shown, a knot or wide object 246 is located at a top end of the string, and the string is passed through a slot 248 connected to drone 200 (only a portion of which is shown in FIGS. 3 and 4), the slot narrower than object 246. A movable arm 250 can be moved by a suitable mechanism, such as an electromechanical actuator (not shown) within drone 200, to push string 244 and wide object 246 out of slot 248 when the weight of drink 240 is detected to have been reduced, for example as coffee drink 240 is grasped and lifted by the recipient user, or as the bag and coffee drink are settled onto a supporting surface. The transfer of the weight of the bag and coffee drink to a supporting surface or to a hand of a user can be detected by a strain gauge or any other sensor, which can be connected to slot 248.

Alternatively arm 250 can have a cutting edge, and can cut string 244. In another variation, string 244 can be made from plastic, and arm 250 can briefly heat string 244 to weaken or cut it. In a yet further variation, slot 248 mechanically actuates to widen, thereby dropping wide object 246 and string 244 from drone 200, whereby bag 242 together with coffee drink 240 are released from drone 200 when it is detected that coffee drink 240 is supported by the recipient user or a supporting surface. In another embodiment, a mechanism within drone 200, such as a mechanical actuator (not shown), can push wide object 246 beyond slot 248 so that wide object 246, together with string 244, can drop out of connection with drone 200, releasing the payload.

Other forms of string release are possible. The length of string 244 can be selected to maintain a desired distance between drone 200 and the coffee recipient during delivery, as well as people and objects below the flight path. Alternatively, as shown in FIG. 4, string 244 can be wound on a spool 252 within drone 200, and coffee drink 240 can be lowered by unspooling string 244 while drone 200 hovers at a safe height, after which string 244 can be cut by a cutter or heating element 254 to be separated from spool 252 at the drone, or string 244 can be separated from the payload by the recipient. It may be prudent for drone 200 to have a means to release string 244 in the event it is inadvertently pulled by a user, potentially disturbing flight stability of drone 200.

While one coffee drink 240 is illustrated, it should be understood that bag 242 can safely contain any number of coffee drinks 240. In a further embodiment, drone 200 is provided with gripper fingers which can grasp a coffee cup, or bag 242, and release them at the appropriate point in time.

FIG. 4 additionally illustrates a heater 258 that can be submerged into coffee drink 240, and is electrically connected to a power source within drone 200, and can be controlled by control circuit 210. When drink 240 is about to be delivered and released, drone 200 can turn off power to heater 258 so that it cools. To conserve energy, circuit 210 can either estimate a temperature of the liquid of coffee drink 240, or can obtain a temperature reading from a sensor associated with heater 258, whereby electrical energy is provided to heater 258 only when the liquid of the drink falls below a predetermined threshold. A lid 260 can be adapted with an aperture 262 through which heater 258 can be inserted or removed. In an alternative embodiment, heater 258 can include a self-contained power source, and heater 258 can sealed within the cup and can be returned after coffee drink 240 is consumed. In a variation, heating element 258 can produce heat by an exothermic reaction, such as by the mixing of two contained chemicals which are advantageously non-toxic, released into contact with each other by bending heating element 258. This heater 258 variation may be sufficiently inexpensive to be discarded after use.

In a variation, drone 200 heating element 258 applies heat to an exterior of the coffee containing vessel, or to an exterior of bag 242, at a temperature which will not burn a human upon contact. In yet another variation, the drone includes or carries an insulating container for the liquid coffee, or the coffee cup. While a heating element can deplete energy from drone 200 quickly, the drone can be recharged automatically by landing at an automatic charging station, or can be provided with a battery replacement system which automatically replaces a depleted battery with a charged battery without human intervention.

Coffee drink 240 can be produced by any known means, whether by an automated coffee maker, a barista, or a combination of a person and a machine. Assembly of drink 240 into holder 230, or with respect to holder 230A, insertion of drink 240 into bag 242, and attachment of string 244, can all be automated using known methods of the coffee making and automation arts. An example of an automated coffee maker that can be used with system 100 is the LAVAZZA BLACK WHITE 2, although many other devices are available, with varying levels of automation. Robotic placement devices can be used to assemble prepared coffee drinks onto holder 230/230A.

It is possible in accordance with the disclosure for: all aspects of coffee production, loading of coffee onto holders, drone flight, selection of individuals having a particular cognitive state such as sleepiness, delivery to such individuals, and reloading of coffee and repeat of the foregoing steps, all without human intervention or assistance.

Coffee characteristics include the caffeine level, for example espresso, regular, or decaffeinated; the temperature; the flavor, for example the style of roasting, the origin of the beans, or an added flavoring; and the addition of sugar or sweetener, or cow, soy, or almond milk or cream. A system of the invention can produce coffee with any of the foregoing characteristics in varying strengths and quantities, and can further coordinate the production of particular styles of coffee drinks, for example espresso, cappuccino, macchiato, filter, or popular regional preparations, such as Cuban, Vietnamese or Turkish styles. Automated systems for producing various types of coffees are known, and these can be integrated within a system 100 of the disclosure, as described herein. Alternatively, people such as baristas or chefs can prepare coffee for delivery by drones.

The disclosure provides for assessing a cognitive characteristic of potential recipients for any of: sleep cycle, bed time for the last N days, a joint measure of the characteristic for two people (e.g. husband and wife), and current blood pressure, or heart rate. The sleep cycle can be determined by accelerometers, video, and other means of motion and movement assessment. System 100 seeks individuals who have a temporarily changed or particular cognitive state, for example due to lack of quality sleep, boredom, or for any other reason. A changed cognitive state can be a cognitive state that does not match a historical cognitive state for an individual engaged in a particular activity. Cognitive states can be saved for users, for example when a user has indicated a preference for tracking, or has approved tracking, of a cognitive state. A particular cognitive state can alternatively be based upon measurements obtained from multiple people, or it can be based upon a programmed profile, and can be associated with people, generally, who are engaged in a particular activity.

System 100 can use input from a calendar, and this can include any of: meeting importance and time, nature and number of people scheduled to be at the meeting, the meeting topic, and forecasted weather, as examples.

The potential recipients can be determined, with a certain confidence, by an estimate of who is in a particular type of room, for example a kitchen or conference room, by an analysis of information from an electronic calendar.

A meeting dynamic can be estimated, which influences the coffee characteristic and coffee demand. For example, if it is known that a meeting participant is meeting with a senior supervisor, and the participant prefers coffee when under stress, the confidence level L can be increased. One or more of such cognitive characteristics can be supplied in a behavioral or preference profile of a user, and such profiles can be consulted for each meeting attendee, where the attendees are reported by the electronic calendar in an automatic system. The profile can include information for a user's physiology and responsiveness to caffeine. In an embodiment, this cognitive information is received from electronic medical records in accordance with appropriate privacy rules. Additionally, the cognitive or medical characteristics can be supplied from a user's medical history, along with prescription medication including information about currently taken medications, and the medication schedule, again according to privacy rules, and/or with the user's permission.

In another embodiment of the disclosure, multiple drones may be in flight, to help with trading of coffee, described elsewhere herein. These drones can consult user profiles of users in an area to improve a probability of having the correctly prepared coffee drinks.

In accordance with the disclosure, a sleep cycle of a user can be determined by accelerometers, video, and other means of motion and movement assessment captured during a sleeping period, as known in the art or hereinafter discovered. The disclosure uses sleep cycle information, in part, so that an assessment of possible drowsiness can be made if a user has had inadequate sleep, or has been awakened during a deep phase of sleep, which may lead to grogginess.

To determine an extent of sleep, and the quality of sleep, system 100 can capture data collected by known or hereinafter developed devices designed for this purpose. Examples include, as reported at LifeHacker.com, the FITBIT ONE device by FitBit of San Francisco, Calif.; the SLEEPASANDROID or SLEEPBOT apps for Android; the JAWBONE UP device, by Jawbone of San Francisco, Calif.; or the SLEEP CYCLE app for iOS.

Prior art approaches to estimating sleep cycle typically make use of monitoring a user's movement during a sleep period. In one additional example, the SLEEP TIME ALARM CLOCK app is executed and the smartphone is placed next to a sleeper on a bed, so that an accelerometer in the smartphone can detect movement, and determine sleeping parameters. This information can be automatically or manually uploaded to system 100, or can be entered into system 100, where it can be used to determine a cognitive state of the user, and therefore the confidence level L can be improved.

In addition a current or forecast cognitive state of a sleeping person, for example a person in bed who may be having meeting soon, can be based on an approach published in U.S. Pat. No. 6,419,629, "Method for predicting human cognitive performance", the contents of which are incorporated by reference herein. This method can facilitate the creation of predicted cognitive performance curves that allow an individual to set their sleep times to produce higher levels of cognitive performance. The method also facilitates the reconstruction of past cognitive performance levels based on sleep history. This data can be used to improve L, as well.

A system of the disclosure can be used in an office building, workshop, or home. The current or forecasted cognitive state of the user can further be based on an assessment of other occupants in a room or bed, a real-time assessment that considers clenching of teeth, snoring, a state of a user and any medications being taken, and a multidimensional vector of cognitive states of a user and people in proximity, for example a spouse.

System 100 can be provided with, or have access to a database of medications which interact with caffeine, such as are published at http://www.drugs.com/drug-interactions/caffeine.html. Further, caffeine can act as bronchodilator and thus improve symptoms for people with asthma (see, for example, http://www.ncbi.nlm.nih.gov/pubmedhealth/PMH0010864/). Thus, when medical records indicate asthma or system 100 detects difficulty breathing, system 100 can optionally speed or prioritize a delivery of coffee to the affected user. Alternatively, caffeine may need to be avoided before certain medical tests, which can be reported to system 100, or determined by system 100 from electronic calendar data, and the drone can therefore avoid that particular user for a proscribed period prior to the test.

Sleep deprivation impairs alertness, cognitive performance, and mood. In addition to serving coffee as described herein, other drink types including caffeine can be served including tea and soft drinks. Additionally, bar drinks containing alcohol can be served, for example at celebrations or parties, and a cognitive state can be assessed as to whether it is prudent to serve an additional bar drink. The cognitive state indicative of excess alcohol can, for certain individuals, resemble sleepiness. Other characteristics, such as unsteadiness or speech changes, can be monitored by one or more drones as described herein. However, in the case of bar drinks, system 100 can determine it is better to not serve an additional drink.

With other caffeinated drinks, and with bar drinks, all of the same cognitive characteristics as described with respect to coffee can be monitored to determine sleepiness, grogginess, drunkenness, or other health characteristic; a user profile can be consulted, which can include favorite drink types; and an electronic calendar can be consulted, and as described elsewhere herein, these elements can be used to determine whether or not to bring a drink by drone. A quantity of caffeine, theine, alcohol, sugar, carbohydrate, calories, or any other level of stimulant, drug, or constituent in a drink is additionally factored into by system 100 as to whether or not it would be healthful, beneficial, or acceptable to deliver a particular drink to a particular user.

Further in accordance with the disclosure, information pertaining to medications currently being taken by a particular user can be compared with the type of drink requested or being offered, and a decision can be made the a particular drink should not be made available to a particular user due to a potentially unhealthful result. In this scenario, the drone can fly away from the user, ignore a summons, or display an indicator light or other indication that the drink is not available to a user. Such avoidance can additionally be carried out with respect to bringing drinks which are unsuitable or prohibited for children.

In an embodiment, system 100 recognizes faces to identify users. One or more cameras mounted in a serving area, or provided upon a drone, can gather images of users in the area. Face recognition can be carried out using any known or hereinafter developed technology, and can include for example deep learning technology, such as is described for example at http://www.cs.toronto.edu/~ranzato/publications/taigman_cvpr14.pdf. Video analytics or other software or electronic processing circuit for carrying out the face recognition can be provided within or carried entirely by the drone, or results of face recognition can be provided to the drone based on video data sent by the drone or a fixed camera to a separate and distinct processing circuit not on the drone. The face recognition can enable the drone to determine an identity of a particular user in an area, and to then bring the correct drink to the user.

Figure 5:
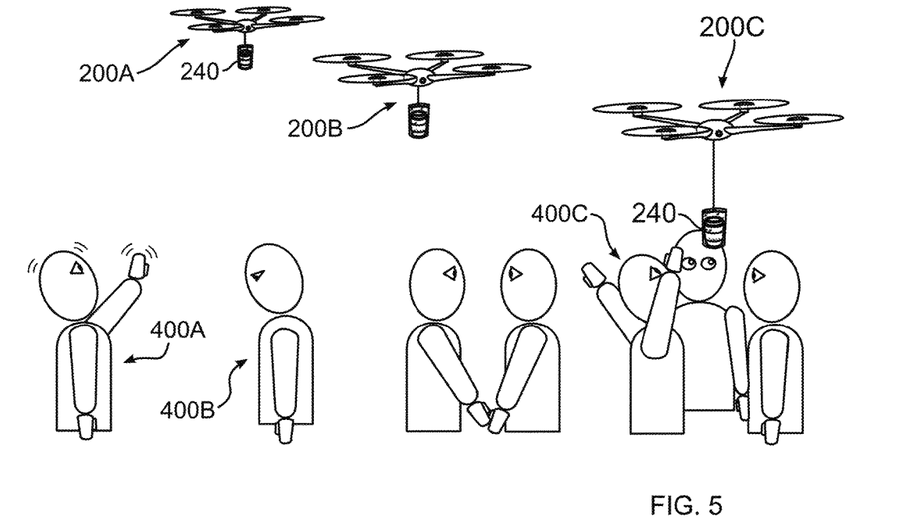
FIG. 5 depicts a plurality of drones of the disclosure delivering stimulating drinks, for example coffee drinks, to individuals within a group, certain individuals indicating with gestures, or indications of a particular cognitive state, a desire for a stimulating drink.

With reference to FIG. 5, in another embodiment, as with facial recognition, the drone can perform some or all of gesture recognition, either sending image data to a server which alerts the drone to particular gestures or instructs the drone to deliver to a particular user making a gesture, or the drone carriers out all such processing on-board. Such gestures can include a nod or hand wave, particularly if the user is looking at the drone. Information regarding gesture recognition can be found at https://en.wikipedia.org/wiki/Gesture_recognition. A hand wave can indicate to bring coffee, or can indicate that coffee is not wanted. System 100 advantageously can discern between a wide variety of such gestures, which can be different among people of various cultures. This is illustrated in FIG. 5, in which user 400A identifies that user 400B appears to be sleepy, and gestures to drone 200B to bring coffee. The gesture in this example includes a raised hand, and a nod of the head and/or hand, while looking in the direction of drone 200B. In response, drone 200B can hover near user 400A until either user 400A or 400B accepts the coffee. After a predetermined interval, if the coffee is not accepted, or if a user performs a gesture interpreted as waiving away drone 200B, drone 200B can leave with the coffee. In an embodiment, drone 200 emits an alarm if the wrong individual intercepts the coffee or other drink.

Also in FIG. 5, user 400C is gesturing in a different manner to user 400A, and is looking in the direction of drone 200C. As with user 400A, the head is tilted backwards, further indicating that the user is directing his attention to a drone. Accordingly, drone 200C approaches to deliver a coffee drink 240.

With further reference to user 400A, system 100 can disambiguated which drone user 400A is addressing, because drone 200A is further away, and system 100 tracks the relative location of drones 200 operating in an area, and is thus aware of their relative locations. Eye gaze direction and body position can further be used by drones 200 to determine which drone 200 user 400A probably expects to reply to the summoning gesture.

In another embodiment, incremental learning is used to improve the effectiveness of visual analytics components. For example, while delivering coffee to a specific person, the drone can acquire new images of users under different viewpoints and lighting, which can facilitate face recognition in future coffee deliveries.

Figure 6:
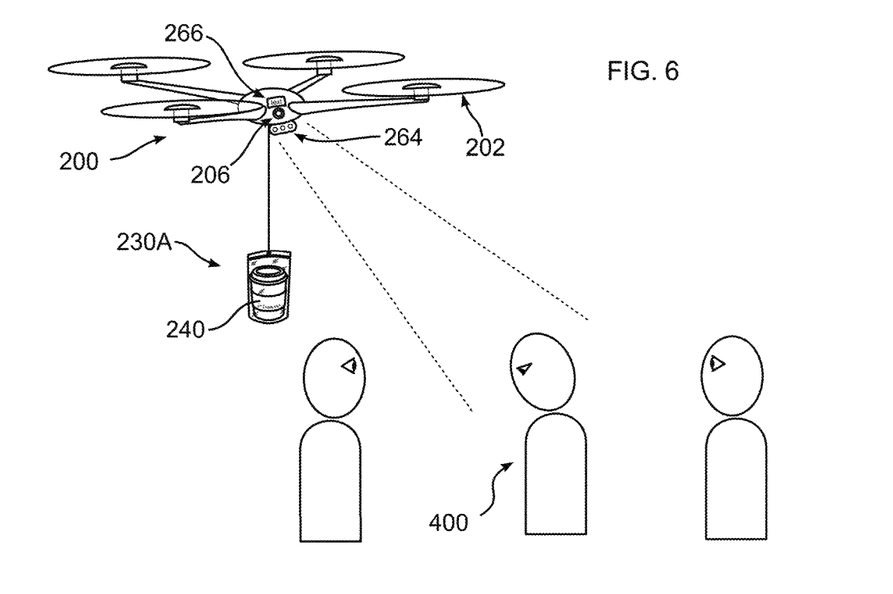
FIG. 6 depicts a drone of the disclosure scanning an individual in group using sensors, and analyzing the sensor data and other data to determine a possibility of a particular cognitive state of the individual as a candidate for delivery of a stimulating drink.

Considering the foregoing, and referring now to FIG. 6, it may be seen that drone 200 is using camera 206 to obtain images of users, in this case of user 400. The image data can be wirelessly transmitted to server 700 for analysis, or can be analyzed aboard drone 200. For simplicity and clarity, for the remainder of this discussion, processing will be described with respect to system 100 which can mean processing is carried out either by drone 200 or server 700, however it should be understood that data analysis and computational processing can be performed in various aspects almost entirely by either server 700 or drone 200, or any portion can be carried out by either device. In an embodiment, all drones in an area can share computational duties using parallel processing, thereby potentially eliminating a need for server 700 in high demand situations.

The image data is processed, in one embodiment, to make an initial assessment of whether user 400 seems tired, and might benefit from a caffeinated drink, such as coffee. Software executing upon a processing circuit of drone 200 or server 700 can recognize certain physical characteristics of a human that are associated with sleepiness or grogginess. In the example of FIG. 4, it may be seen that a head of user 400 is angled downwards, indicating impending sleep, or a lack of attention to surroundings. A posture of other users in the area can be compared with a particular user, to see if the observed posture is different. However, a downwards angled head can also indicate reading or observing something at a lower position. Another indication of sleepiness is drooping or closing eyelids, also evident in FIG. 6, particularly as compared with other users. As discussed further below, images of user 400 from a profile of user 400 can provide further indication of what user 400 normally looks like when in an attentive state, and these stored images can be compared with images currently obtained.

These initial clues to sleepiness form an initial determination of confidence level (L), but the value of L may still be too low to warrant a delivery of coffee, in accordance with a predetermined threshold. To increase L, system 100 can now attempt to learn the identify of user 400, so that system 100 can access data corresponding to profile information of user 400. The profile information can be cached in data storage within control circuit 220, or a processing circuit within circuit 220 can cause transmission of a request for profile data from server 700.

A determination of an identity of user 400 can be carried out using face recognition, as described elsewhere herein. Alternatively, all attendees at an event can be provided with an electronic tag, such as an RFID tag, which is encoded with identity information, and a corresponding tag reader connected to drone 200 can interrogate a tag of the user for the identification. In a variation, drone 200 can use a BLUETOOTH protocol to obtain identifying information from a smartphone of user 400. In another variation, system 100 can use a speaker connected to drone 200 to audibly ask user 400 what his name is, and can use a microphone connected to drone 200 to obtain an answer from user 400, whereupon voice recognition can be used to identify user 400.

Once system 100 has obtained profile data, it may determine whether user 400 is eligible for coffee, and is not excluded due to age, medical condition, medicine usage, or any other reason. If it is determined from the profile that user 400 is eligible for coffee, and it is also determined that user 400 likes coffee, and particularly likes the coffee that drone 200 is transporting, further analysis can be carried out.

For example, system 100 can examine the profile of user 400 to determine if user 400 has experienced poor sleep in the recent past. If this data is not available in the profile, system 100 can determine if sleep data is available from any other source, for example FitBit data uploaded to a location accessible to system 100. Sleep data may also be available from an application which has collected such data on a smartphone of user 400. Further, user 400 may have installed an application of system 100 on her phone, which has either collected sleep data, or has permission to obtain sleep data from another application, and the system 100 app can obtain this data and transmit it to system 100, for example with a nearfield or BLUETOOTH transmission to drone 200.

Sleep data can be analyzed in accordance with U.S. Pat. No. 6,419,629, for example, and the formula M=m(t) or $M_1=F+A_1*\cos(2Pi(t-V_1)/P_1)+A_2*\cos(2Pi(t-V_2)/P_2)$, as described therein can be used to enable the creation of predictive cognitive performance curves for a user. If the prediction is for poor performance due to sleep quality issues, L is increased. For this method, it may be necessary to first obtain data for the user relating to cognitive ability under controlled conditions, although if such data is unavailable, data from other individuals can be used to enable an estimated predictive cognitive capacity for a particular user herein.

Once sleep data has been obtained, it may be determined if user 400 has had sleep quality problems recently, and if cognitive capability is likely to be impaired, and if so, this can increase the value of L sufficiently to warrant an offer of coffee relative to other users. Other parameters can be probed as described herein, including biometric parameters. For example, drone 200 can be provided with sensors that can determine any or all of a heart rate, blood pressure, blood oxygen saturation, pupil dilation, breathing rate, skin temperature, a chemical composition of breath of user 400, an extent of movement of user 400, or any other physical parameters which can be analyzed for tiredness, sleepiness, or grogginess, and which can further increase a value of L, until a threshold parameter is reached for an offer of coffee. It can be advantageous to use at least two of the physiological parameters to increase an accuracy of a determination of L. Advantageously, the biometric parameters can be evaluated without contact with, or interruption to, the user. Sensors, a microphone, and a speaker are depicted as attached to drone 200 in FIG. 5, in this example located upon a pod 264. A display 266 is also illustrated.

Ultimately, if the value of L is otherwise satisfied, or almost satisfied, system 100 can optionally use a speaker and microphone connected to drone 200 to ask user 400 if they would like a cup of coffee. Communication with user 400, for example for confirmation of a desire for coffee, can alternatively be carried out by a text message or voice call from system 100 to a smartphone of user 400, which user 400 can respond to, or system 100 can display text or symbols upon a display connected to drone 200, and user 400 can gesture or speak a response to the drone 200.

If it is determined that coffee is to be provided to user 400, it may be that the nearest drone does not have coffee which matches the preference of user 400, as determined from a profile of user 400, or based upon communication with user 400 by any of the aforedescribed means. Accordingly, a nearby drone carrying the correct style of drink can be summoned by system 100 or a gesture of user 400 to deliver a desired drink to user 400. Alternatively, a drone 200 can return to a supply area and obtain the correct drink for user 400.

In a further embodiment, system 100 can serve as a trans-vendor service that performs auctions of coffee offerings, which can be bundled, and which can include multiple drone deliveries. More particularly, a coffee producer can hire or license system 100 for an event or ongoing service at a particular location. Likewise, drones of system 100 can serve not only coffee or other drink as described herein, but can deliver companion products such as snacks, hors d'oeuvres, or even non-food items.

Additionally, system 100 can receive and fulfill a request for a group or series of coffee drinks. System 100 can provide a means for obtaining descriptions of available coffee drinks, their prices, and current demand, which could be based on location, cognitive state of users in a crowd, and a context of the assembly. In an embodiment, a QR code appears on the drone, or a website address, and users can scan the code or go to the website address, where they can enter a drink order, take a photo of their face so they can be recognized, or otherwise register, enter profile information, or interact with system 100.

System 100 can include or be offered as part of an auction, or coffee/drone broker, which optimizes the distribution of selected drinks throughout a crowd. In this manner, those valuing coffee service most highly can outbid others, particularly where capacity is limited for any reason. The auction can be carried out by any known method, including for example English, Dutch, or Vickrey styles. System 100, and the auction, can be operated within an electronic communication 'Cloud', which can be private, public, a hybrid of both, community, distributed, multicloud, or other style.

System 100 can utilize monetary or digital currency bids, but can also enable the trading of coffee drinks. This can include system 100 recognizing that two or more users do not want the style of drink served to them, and exchanging unopened and rejected drinks among such users to avoid waste. System 100 can further detect when users want to share a beverage, and can bring an extra empty cup for this purpose. Similarly, system 100 can reroute a drink at a user's request, or can deliver a drink to one user that has been ordered by another user. Alternatively, when a desired beverage is not available, system 100 can suggest a drink which is the closest available match, and deliver such a drink to a user, if indicated to be acceptable.

Example Computing System

Figure 7:
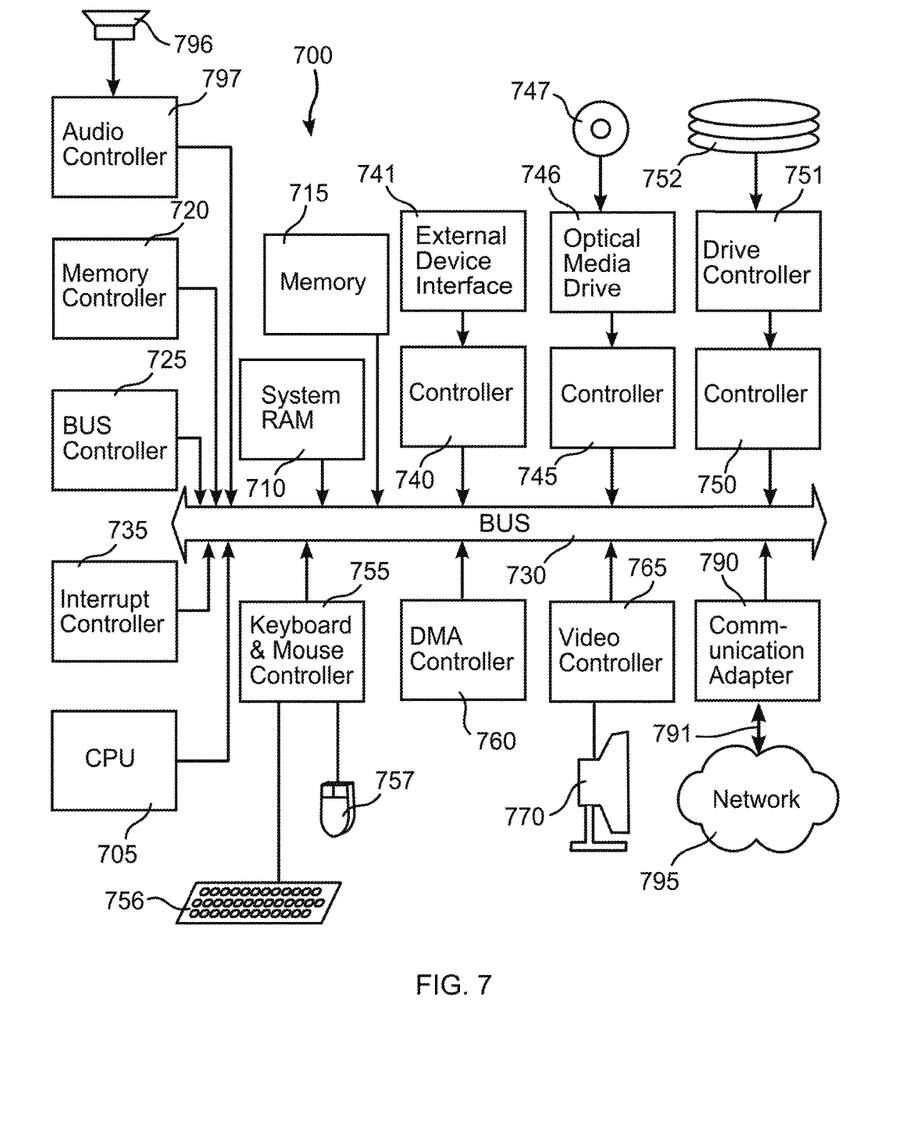
FIG. 7 depicts a computer system having components, some or all of which can be used as part of a drone or server when carrying out the disclosure.

FIG. 7 illustrates the system architecture for a computer system 700 which can be a computer server, and which can include the functions of a process controller, or other processor on which or with which the disclosure may be implemented. The exemplary computer system of FIG. 7 is for descriptive purposes only. Although the description may refer to terms commonly used in describing particular computer systems, the description and concepts equally apply to other systems, including systems having architectures dissimilar to FIG. 7. Computer system 700 can control temperatures, motors, pumps, flow rates, power supplies, ultrasonic energy power generators, and valves, using actuators and transducers. One or more sensors, not shown, provide input to computer system 700, which executes software stored on non-volatile memory, the software configured to received inputs from sensors or from human interface devices, in calculations for controlling system 200.

Computer system 700 includes at least one central processing unit (CPU) 705, or server, which may be implemented with a conventional microprocessor, a random access memory (RAM) 710 for temporary storage of information, and a read only memory (ROM) 715 for permanent storage of information. A memory controller 720 is provided for controlling RAM 710.

A bus 730 interconnects the components of computer system 700. A bus controller 725 is provided for controlling bus 730. An interrupt controller 735 is used for receiving and processing various interrupt signals from the system components.

Mass storage may be provided by DVD ROM 747, or flash or rotating hard disk drive 752, for example. Data and software, including software of the disclosure, may be exchanged with computer system 700 via removable media such as diskette, CD ROM, DVD, Blu Ray, or other optical media 747 connectable to an Optical Media Drive 746 and Controller 745. Alternatively, other media, including for example a media stick, for example a solid state USB drive, may be connected to an External Device Interface 741, and Controller 740. Additionally, another computing device can be connected to computer system 700 through External Device Interface 741, for example by a USB connector, BLUETOOTH connector, Infrared, or WiFi connector, although other modes of connection are known or may be hereinafter developed. A hard disk 752 is part of a fixed disk drive 751 which is connected to bus 730 by controller 750. It should be understood that other storage, peripheral, and computer processing means may be developed in the future, which may advantageously be used with the disclosure.

User input to computer system 700 may be provided by a number of devices. For example, a keyboard 756 and mouse 757 are connected to bus 730 by controller 755. An audio transducer 796, which may act as both a microphone and a speaker, is connected to bus 730 by audio controller 797, as illustrated. It will be obvious to those reasonably skilled in the art that other input devices, such as a pen and/or tablet, Personal Digital Assistant (PDA), mobile/cellular phone and other devices, may be connected to bus 730 and an appropriate controller and software, as required. DMA controller 760 is provided for performing direct memory access to RAM 710. A visual display is generated by video controller 765 which controls video display 770. Computer system 700 also includes a communications adapter 790 which allows the system to be interconnected to a local area network (LAN) or a wide area network (WAN), schematically illustrated by bus 791 and network 795.

Operation of computer system 700 is generally controlled and coordinated by operating system software, such as a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 705 coordinates the operation of the other elements of computer system 700. The present disclosure may be implemented with any number of commercially available operating systems.

One or more applications, such as an HTML page server, or a commercially available communication application, may execute under the control of the operating system, operable to convey information to a user.

Example Mobile Computing System

Figure 8:
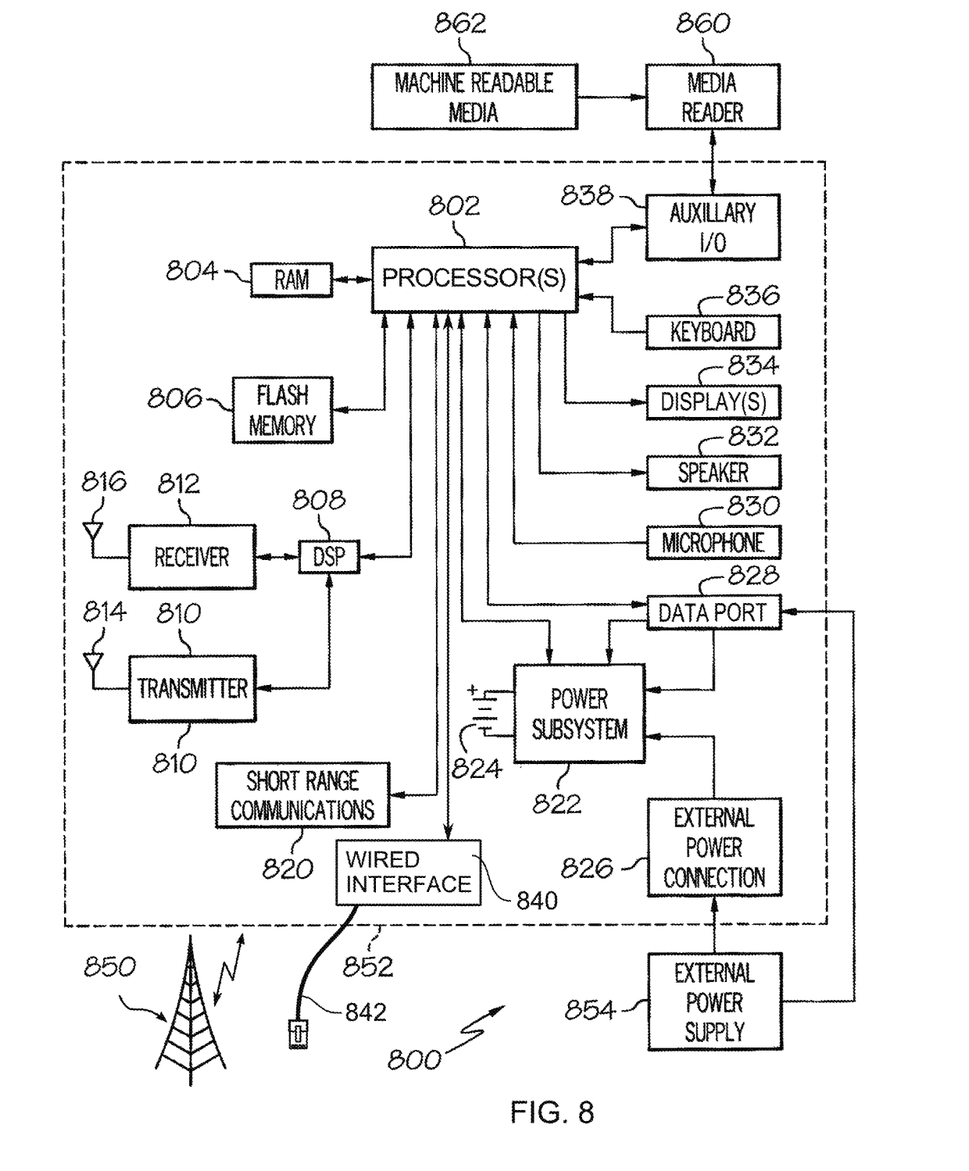
FIG. 8 depicts a mobile computing system having components, some or all of which can be used as part of a drone or server when carrying out the disclosure.

FIG. 8, is a block diagram of an electronic device and associated components 800, which can be used in carrying out the disclosure. Drone 200 can include one or all of the components of device 800. In this example, an electronic device 852 is a wireless two-way communication device with voice and data communication capabilities. Such electronic devices communicate with a wireless voice or data network 850 using a suitable wireless communications protocol. Wireless voice communications are performed using either an analog or digital wireless communication channel. Data communications allow the electronic device 852 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated electronic device 852 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate.

The electronic device 852 includes a microprocessor 802 that controls the overall operation of the electronic device 852. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

A battery 824 is connected to a power subsystem 822 to provide power to the circuits of the electronic device 852. The power subsystem 822 includes power distribution circuitry for providing power to the electronic device 852 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the electronic device 852.

The data port 828 of one example is a receptacle connector 104 or a connector that to which an electrical and optical data communications circuit connector 800 engages and mates, as described above. The data port 828 is able to support data communications between the electronic device 852 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the device by enabling information or software exchange through direct connections between the electronic device 852 and external data sources rather than via a wireless data communication network. In addition to data communication, the data port 828 provides power to the power subsystem 822 to charge the battery 824 or to supply power to the electronic circuits, such as microprocessor 802, of the electronic device 852.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the electronic device 852. A predetermined set of applications that control basic device operations, including at least data and voice communication applications, is able to be installed on the electronic device 852 during manufacture. Examples of applications that are able to be loaded onto the device may be a personal information manager (PIM) application having the ability to organize and manage data items relating to the device user, such as, but not limited to, e-mail, calendar events, voice mails, appointments, and task items.

Further applications may also be loaded onto the electronic device 852 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the electronic device 852 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the electronic device 852 is substantially similar, except that received signals are generally provided to a speaker 832 and signals for transmission are generally produced by a microphone 830. Alternative voice or audio I/O subsystems, such as a voice message recording subsystem, may also be implemented on the electronic device 852. Although voice or audio signal output is generally accomplished primarily through the speaker 832, the display 834 may also be used to provide an indication of the identity of a calling party, the duration of a voice call, or other voice call related information, for example.

Depending on conditions or statuses of the electronic device 852, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the electronic device 852 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above. A wired interface 840 and connector 842 can be provided, configured to support any known wired communication protocol, for example USB.

A media reader 860 is able to be connected to an auxiliary I/O device 838 to allow, for example, loading computer readable program code of a computer program product into the electronic device 852 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the electronic device through the Data port 828 or computer readable program code is alternatively able to be provided to the electronic device 852 through the wireless network 850. Sensors 870 can be provided either internal or external to a housing of device 300/800, of any of the various types and functions as described herein.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method for delivering a drink to an individual, comprising:
   connecting the drink to an unmanned aerial vehicle (UAV);
   flying the UAV to an area including a plurality of people;
   scanning the people, using one or more sensors connected to the UAV, the one or more sensors connected to an electronic processing circuit which identifies an individual among the people that may have a predetermined sleepy cognitive state including determining a confidence level corresponding to a probable desire of the individual for the drink including a stimulant which reduces a sleepy cognitive state, based on the sensor data and using sleep data pertaining to sleep experienced by the people when selecting the individual that may have the sleepy cognitive state;

accessing sleep data pertaining to a sleep cycle of the individual determined by motion detection of the individual during a sleep period, and adjusting the confidence level in accordance to the sleep data; and if the confidence level reaches a predetermined level, flying the UAV to the individual that may have the sleepy cognitive state to deliver the drink including the stimulant to the individual.

2. The method of claim 1, wherein the UAV is fully autonomous, and flies to the area and flies to the individual without human assistance.

3. The method of claim 1, wherein the electronic processing circuit is on the UAV.

4. The method of claim 1, wherein the electronic processing circuit is not on the UAV, and the UAV transmits sensor data wirelessly to the electronic processing circuit to identify the individual.

5. The method of claim 1, where the drink includes coffee.

6. The method of claim 1, wherein the electronic processor circuit determines an individual that may have a predetermined cognitive state by examining a physiological state of the individual determinable using the sensor data.

7. The method of claim 1, wherein scanning the people includes obtaining images of the people, the images being analyzed to determine an angular disposition of at least one of the head, eyes, back, and shoulders of one or more of the people.

8. The method of claim 6, wherein the sensor data includes one or more of heart rate, blood pressure, pupil dilation, breathing rate, skin temperature, and a chemical composition of breath, of at least one of the people.

9. The method of claim 6, wherein the sensor data includes one or more of biometrics, blood pressure, and facial expression analysis.

10. The method of claim 1, wherein the electronic processor circuit uses sensor data to determine an identity of one or more of the people.

11. The method of claim 1, wherein the electronic processor circuit uses image data of one or more of the people to determine an identity of an individual using a face recognition algorithm.

12. The method of claim 1, wherein the electronic processing circuit accesses electronic calendar data relating to one or more of the people, and determines a likelihood that an individual among the people may have a predetermined cognitive state using meeting schedules of individuals among the people.

13. The method of claim 1, wherein if the individual identified rejects the delivered drink, the UAV selects another individual for delivery of the drink.

14. The method of claim 1, wherein a plurality of the people have provided informational profiles including data relating to a sleep state.

15. The method of claim 1, wherein the sensor data is analyzed by the electronic processor circuit to identify a gesture of at least one of the people indicating a desire for the drink.

16. The method of claim 1, wherein delivering the drink to the individual includes lowering the drink to the individual on a string.

17. The method of claim 1, wherein the motion detection is carried out using at least one of an accelerometer and camera.

* * * * *